United States Patent [19]

Rocher et al.

[11] Patent Number: 5,446,059
[45] Date of Patent: Aug. 29, 1995

[54] BENZIMIDAZOLE-DERIVED COMPOUNDS, METHOD FOR PREPARING THE SAME, AND THERAPEUTICAL AND COSMETIC USES THEREOF

[75] Inventors: Jean-Philippe Rocher, Gaillard; Daniel Cavey, Valbonne, both of France

[73] Assignee: Centre International de Recherches Dermatologiques Galderma (CIRD Galderma), Valbonne, France

[21] Appl. No.: 142,464

[22] PCT Filed: May 29, 1992

[86] PCT No.: PCT/FR92/00482
§ 371 Date: Jan. 10, 1994
§ 102(e) Date: Jan. 10, 1994

[87] PCT Pub. No.: WO92/21663
PCT Pub. Date: Dec. 10, 1992

[30] Foreign Application Priority Data
May 31, 1991 [FR] France .................. 91 06583

[51] Int. Cl.$^6$ .................. C07D 235/18; A61K 31/415
[52] U.S. Cl. .................. 514/374; 548/310.1
[58] Field of Search .......... 548/310.1, 310.7; 514/394

[56] References Cited

U.S. PATENT DOCUMENTS

| | | | |
|---|---|---|---|
| 4,717,720 | 1/1988 | Shroot et al. | 514/569 |
| 4,920,140 | 4/1990 | Shroot | 514/394 |
| 4,940,696 | 7/1990 | Shroot et al. | 514/423 |
| 5,098,895 | 3/1992 | Shroot et al. | |

FOREIGN PATENT DOCUMENTS

| | | |
|---|---|---|
| 0199636 | 10/1986 | European Pat. Off. |
| 2570377 | 3/1986 | France. |
| 2164648 | 3/1986 | United Kingdom. |

OTHER PUBLICATIONS

Katritzky, Comprehensive Heterocyclic Chemistry p. 472 (1984).

*Primary Examiner*—Robert Gerstl
*Attorney, Agent, or Firm*—Oliff & Berridge

[57] ABSTRACT

Benzimidazole derivatives having general formula (I), wherein $R_1$ and $R_2$ are a hydrogen atom, a lower alkyl radical, an $OR_4$ radical, a lower fluoroalkyl radical or a halogen atom; $R_3$ is a hydrogen atom, a lower alkyl radical, a halogen, a hydroxyl or a lower alkoxy radical having 1-6 carbon atoms; $R_4$ is a hydrogen atom, a lower alkyl radical, a benzyl radical or a (II) radical, $PO_3H$, $SO_3H$ or an aminoacid residue; $R_7$ is a lower alkyl radical, a lower alkoxy radical having 1-6 carbon atoms, a $-(CH_2)_n-COOH$ radical where $n=1-6$, or the radical (III), where $r'$ and $r''$ are a hydrogen atom or a lower alkyl radical, or form, together with the nitrogen atom, a 5 or 6-membered heterocyclic ring optionally interrupted by a heteroatom; $R_5$ and $R_6$ are different and represent the $OR_8$ radical or a mono or polycyclic cycloalkyl radical having 5–12 carbon atoms bound to the phenyl core by a tertiary carbon; $R_8$ is a hydrogen atom, a lower alkyl radical, an acyl radical having 2–7 carbon atoms, a benzyl radical optionally substituted by one or more halogen atoms, or a benzoyl radical; and salts of said compounds obtained by adding a pharmaceutically acceptable acid or base. Said compounds may be used therapeutically, in particular in relation to inflammatory and/or immunoallergic conditions, and cosmetically to provide body and hair care.

16 Claims, No Drawings

BENZIMIDAZOLE-DERIVED COMPOUNDS, METHOD FOR PREPARING THE SAME, AND THERAPEUTICAL AND COSMETIC USES THEREOF

The subject of the present invention is new benzimidazole derivatives, method for preparing the same and therapeutical and cosmetic uses thereof.

These new benzimidazole derivatives have proved to have, in human or veterinary medicine, good activity with respect to inflammatory and/or immunoallergic conditions.

In cosmetics, these new benzimidazole derivatives constitute particularly advantageous substances in body and hair hygiene.

The state of the art relating to benzimidazole derivatives is essentially represented by French Patent Application No. 85 13747 (2,570,377) which describes certain benzimidazole derivatives having a biological profile assigning them to the compounds known under the name of "retinoid" and having a reinforced activity in the treatment of dermatological ailments linked to a keratinization disorder (differentiation/proliferation).

The benzimidazole derivatives according to the invention can be represented by the following general formula:

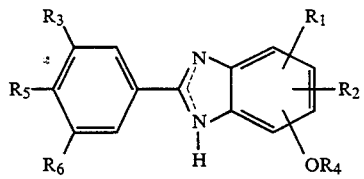 (I)

in which:

$R_1$ and $R_2$ represent a hydrogen atom, a lower alkyl radical, an $OR_4$ radical, a lower fluoroalkyl radical or a halogen atom, $R_3$ represents a hydrogen atom, a lower alkyl radical, a halogen, a hydroxyl or a lower alkoxyradical having from 1 to 6 carbon atoms, $R_4$ represents a hydrogen atom, a lower alkyl radical, a benzyl radical, or a

$PO_3H$ or $SO_3H$ radical or an amino acid residue, $R_7$ represents a lower alkyl radical, a lower alkoxy radical having from 1 to 6 carbon atoms, the $-(CH_2)_n-COOH$ radical, $n=1$ to 6, or the

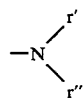

radical, r' and r" representing a hydrogen atom or a lower alkyl radical or r' and r", taken together, form, with the nitrogen atom, a 5- or 6-membered heterocycle optionally interrupted by a heteroatom, $R_5$ and $R_6$, which are different, represent the $OR_8$ radical or a mono- or polycyclic cycloalkyl radical having from 5 to 12 carbon atoms, linked to the phenyl ring via a tertiary carbon;

$R_8$ represents a hydrogen atom, a lower alkyl radical, an acyl radical having from 2 to 7 carbon atoms, a benzyl radical optionally substituted by one or a number of halogen atoms or the benzoyl radical, and the salts of the said compounds obtained by addition of a pharmaceutically acceptable acid or base.

According to the invention, the salts are obtained by addition of a base when $R_4$ represents $SO_3H$, $PO_3H$ or $-CO(CH_2)_n-COOH$. These salts can also be obtained by addition of an acid when $R_5$ represents the

radical, r' and r", taken together forming a basic heterocycle.

It is also possible to form salts by addition of an acid to the nitrogen atoms of the benzimidazole system.

Lower alkyl radical must be understood to mean a linear or branched radical having from 1 to 6 carbon atoms, especially a methyl, ethyl, isopropyl, butyl, 1-methylpropyl, 1-ethylpropyl, tert-butyl, 1,1-dimethylpropyl and 1-methyl-1-ethylpropyl radical.

Lower fluoroalkyl radical must be understood to mean a radical having from 1 to 6 carbon atoms and from 1 to 5 fluorine atoms, such as the trifluoromethyl radical.

The halogen atom is according to the invention preferably a chlorine, bromine or fluorine atom.

Lower alkoxy radical having from 1 to 6 carbon atoms must be understood to mean especially a methoxy, ethoxy, isopropoxy or butoxy radical.

Mono- or polycyclic cycloalkyl radical, having from 5 to 12 carbon atoms, linked to the phenyl ring via a tertiary carbon, must be understood to mean especially 1-adamantyl or 1-methylcyclohexyl radicals.

Acyl radical, having from 2 to 7 carbon atoms, must be understood to mean especially acetyl, propionyl, butyryl, isobutyryl, valeryl or pivalyl radicals.

When r' and r", taken together, form, with the nitrogen atom, a 5- or 6-membered heterocycle, the latter is preferably a piperidino, morpholino, pyrrolidino or piperazino radical, optionally substituted in position 4 by a lower alkyl radical.

Amino acid residue must be understood to mean more particularly residues deriving from lysine, glycine or aspartic acid, the latter being linked to the benzene ring via an ester functional group.

The following may especially be mentioned among the compounds of formula (I) above:
4-hydroxy-2-[3-(1-adamantyl)-4-hydroxyphenyl]benzimidazole,
5-hydroxy-2-[3-(1-adamantyl)-4-hydroxyphenyl]benzimidazole,
5-benzyloxy-2-[3-(1-adamantyl)-4-methoxyphenyl]benzimidazole,
5-hydroxy-2-[3-(1-adamantyl)-4-methoxyphenyl]benzimidazole,
5-benzyloxy-2-[3-(1-methylcyclohexyl)-4-(benzyloxy)phenyl]benzimidazole,
5-hydroxy-2-[3-(1-methylcyclohexyl)-4-hydroxyphenyl]benzimidazole, 5-methoxy-2-[3-(1-adamantyl)-4-(benzyloxy)phenyl]-benzimidazole, 5-methoxy-2-[3-(1-adamantyl)-4-hydroxyphenyl]benzimidazole, 5-benzyloxy-2-[3 -benzyloxy-4-(1-adamantyl)phenyl]-benzimidazole, 5-hydroxy-2-[3-hydroxy-4-(1-adamantyl)phenyl]benzimidazole, 5-benzyloxy-2-[3-(1-adamantyl)-4-benzyloxy-5-methoxyphenyl]benzimidazole, 5-hydroxy-2-[3-(1-adamantyl)-4-hydroxy-5-methoxyphenyl]benzimidazole, 5-benzyloxy-2-[3-(1-adamantyl)-4-(benzyloxy)phenyl]-benzimidazole, 5-methoxy-2-[3-(1-adamantyl)-4-methoxyphenyl]benzimidazole, 5-acetoxy-2-[3-(1-adamantyl)-4-acetoxyphenyl]benzimidazole, 5-acetoxy-2-[3-(1-adamantyl)-4-hydroxyphenyl]benzimidazole, Another subject of the present invention is the process for the preparation of the compounds of formula (I).

Various synthetic methods allow access to the compounds of formula (I) but it is preferable according to the invention to use the following methods:

According to the first method, an aromatic carboxylic acid derivative of formula (1) is condensed with an aromatic orthodiamine of formula (2) according to Reaction Scheme (A) below:

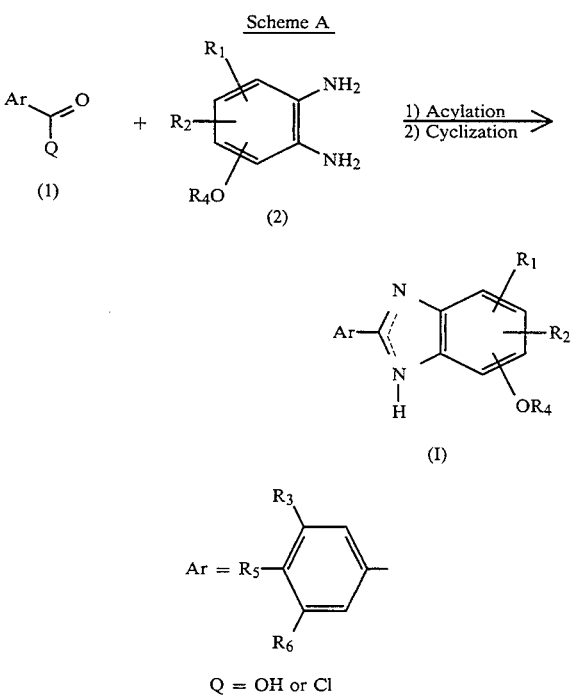

Q = OH or Cl

The acylation reaction is carried out conventionally by using the compound of formula (1) in the acid chloride form in the presence of a tertiary amine in THF.

The cyclization reaction is carried out by heating the reaction mixture at reflux under a nitrogen atmosphere in the presence of an aromatic solvent such as toluene or xylene, a reagent such as paratoluenesulphonic acid or phosphorus oxychloride being used.

According to a second, more particularly preferred, method, an aromatic carboxylic acid derivative of formula (1), which is dissolved in dichloromethane or in toluene, is reacted, in a first step, with an orthonitroaniline of formula (3) in pyridine at the reflux temperature of the solvent having the lowest boiling point (40° to 100° C.). The intermediate compound obtained (4) is then reduced by catalytic hydrogenation (5% palladium-on-charcoal) or by using a metal salt such as tin chloride in THF and is then cyclized as shown above for the method according to Scheme A.

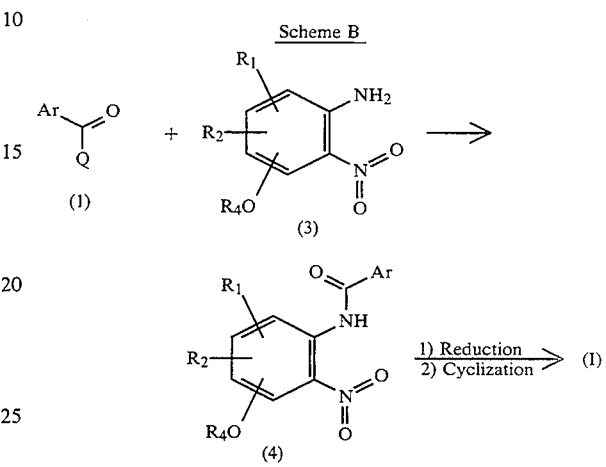

When the substituents of the aromatic part and/or of the heterocyclic part of the compound of formula (I) are hydroxyl functional groups, a prior protection of this functional group must be carried out in the ester form or in the form of an alkoxy or benzyloxy derivative. In these cases, after the cyclization reaction, an additional deprotection stage is necessary. It can be carried out by hydrogenolysis in the presence of a palladium catalyst in the case of a benzyl substituent, by a Lewis acid such as $AlCl_3$ or $BBr_3$ or by pyridine hydrochloride in the case of an alkyl or benzyl substituent, or by saponification if the phenol functional group is protected in the ester form. Deprotection methods catalyzed by transition metals such as palladium or rhodium can also be used.

The hydroxyl functional groups can be converted to esters, carbamic esters, sulphonic esters or phosphonic esters or alkylated according to conventional processes; these analogues correspond to the various meanings given to the $R_4$ radical.

Another subject of the present invention is, as medicament, the compounds of general formula (I) as defined above.

The compounds according to the invention in particular show good activity in the tests:

a) of inhibition of inflammation (oedema of the ear) induced by the topical application of arachidonic acid in mice, b) of inhibition of contact allergy (oedema of the ear) induced by the topical application of oxazolone in mice.

These tests are respectively accepted as measurements of anti-inflammatory activity and of immunodependant anti-inflammatory activity.

The compounds according to the invention very particularly find an application in human or veterinary medicine for the preparation of medicaments intended for the treatment or the prevention of inflammatory and/or immuno-allergic conditions.

These medicaments are particularly suitable for treating atopic dermatitis, seborrhoeic dermatitis, dermatitis due to irritants, neurodermatitis, eczema of various origins, nappy rash, erythroprosopalgia, rosacea, ichthyosis, psoriasis, lichen planus, prurigo and insect stings or bites.

They can also be used in cases of arthritis, synovitis, tendinitis or sprain and in all post-traumatic or rheumatological inflammatory conditions.

They can also be indicated in the case of inflammation of the ENT region (rhinitis), ophthalmic inflammation (conjunctivitis or eczema of the eyelids, for example) and inflammation of the mucous membranes (gingivitis, stomatitis, vulvitis, and the like).

The compounds of the invention can also be used, as medicaments, as adjuvants in the aetiologic treatment of inflammatory dermatosis of infectious or parasitic origin and as adjuvant in anti-acne treatment.

The compounds according to the invention also find an application in body and hair hygiene and in the prevention (photoprotection) and treatment of solar erythema, in the prevention of photoinduced cutaneous inflammation (optionally in combination with other photoprotectors) or also in the protection of the skin against solvents or primary irritants. The compositions according to the invention can also be used in the form of an anti-irritant cream for sensitive skins.

Another subject of the present invention is thus new medicinal compositions intended in particular for the treatment of the abovementioned ailments, characterized in that they contain, in a pharmaceutically acceptable vehicle, at least one compound of formula (I).

Administration can be carried out enterally, parenterally or locally (topically: skin or mucous membrane or ocular).

The compounds according to the invention are generally administered enterally or parenterally at a daily dose of 0.01 to 100 mg/kg of body weight.

The oral compositions can be provided, for example, in the form of tablets, of gels, of dragées, of syrups, of suspensions, of solutions, of powders, of granules or of emulsions or also of lipid or polymer vesicles, nanospheres or microspheres, making possible a controlled release of the active principle.

The local compositions generally contain between 0.005% and 10% by weight of compound of formula (I) according to the invention.

The topical compositions are provided in particular in the form of ointments, of creams, of milks, of salves, of powders, of gingival pastes, of impregnated pads, of solutions, of lotions, of gels, of sprays, of shampoos, of washing lotions or also of lipid or polymer vesicles or nanospheres or microspheres, of polymer patches or hydrogels making possible a controlled release of the active principle.

The compositions administered ocularly are mainly eyewashes.

The compositions administered nasally can be provided mainly in the aerosol form.

Another subject of the present invention is a new cosmetic composition intended to prevent or correct the unattractive appearance of the skin caused by inflammatory conditions. The cosmetic compositions according to the invention generally contain from 0.001 to 5% by weight of compound of formula (I).

The cosmetic compositions are provided in the same form as the pharmaceutical compositions for the topical route.

All these pharmaceutical or cosmetic forms are prepared according to the standard methods.

The medicinal and cosmetic compositions according to the invention can contain inert or even pharmacologically or cosmetically active additives and in particular: hydrating agents such as thiamorpholinone and its derivatives or urea, vitamins such as vitamin A, E or F or their derivatives, antiseborrhoeic agents such as S-(carboxymethyl)cysteine, S-benzylcysteamine and their derivatives, or tioxolone, anti-acne agents such as retinoic acid and its derivatives or 6-[3-(1-adamantyl)-4-methoxyphenyl]-2-naphthoic acid and its analogues, antibiotics such as erythromycin and its esters, neomycin or the tetracyclins, antifungal compounds such as the 4,5-(polymethylene) isothiazolinones or the pyrithione derivatives, agents promoting hair regrowth, such as "Minoxidil" (2,4-diamino-6-piperidinopyrimidine 3-oxide) and its derivatives, Diazoxide (7-chloro-3-methyl-1,2,4-benzothiadiazine 1,1-dioxide), Phenytoin (5,5-diphenyl-2,4-imidazolidinedione) and oxapropanium iodide, other nonsteroidal anti-inflammatory agents such as N-benzylphenyl-α-acetoxyacetamide, polyunsaturated fatty acid derivatives such as 5,8,11-eicosatriynoic acid and 5,8,11,14-eicosatetraynoic acid, their esters and their amides, antihistamines such as promethazine or cinnarizine, antipruritic compounds such as palmitoyl-collagenic acid, antipsoriatic agents such as anthralin and its derivatives, or photoprotective agents such as UV-A and UV-B screening agents.

The compositions according to the invention can also contain flavour-improving agents, preserving agents, stabilizing agents, moisture-regulating agents, pH regulating agents, agents for modifying osmotic pressure, emulsifying agents, UV-A and UV-B screening agents, and antioxidizing agents such as α-tocopherol, butylhydroxyanisole or butylhydroxytoluene.

PREPARATION EXAMPLES

Example 1

4-Hydroxy-2-[3-(1-adamantyl)-4-hydroxyphenyl]benzimidazole a) 2-Benzyloxy-6-nitroaniline 6.16 g (40 mM) of 2-amino-3-nitrophenol, 60 ml of dimethylformamide and 6.62 g (48 mM) of dipotassium carbonate are introduced into a round-bottomed flask. 4.75 ml (40 mM) of benzyl bromide are then added dropwise and the reaction mixture is brought to 80° C. After having been stirred under an inert atmosphere for 1.5 hours, the mixture is poured into ice-cold water and then extracted with 200 ml of ethyl acetate. The organic phase is separated by settling and, after washing with a saturated sodium chloride solution, it is dried over magnesium sulphate and evaporated to dryness. The product is chromatographed on a silica column (eluent: 10% ethyl acetate and 90% hexane) to lead to 8.8 g (90%) of the expected compound in the form of an orangey oil.

b) 6-Amino-2-(benzyloxy)aniline 7.32 g (30 mM) of the above product, 70 ml of ethanol and 28.44 g (150 mM) of tin dichloride are introduced, under an inert atmosphere, into a round-bottomed flask. After addition of 4.5 ml of concentrated hydrochloric acid, the mixture is brought to reflux for 3 hours. The mixture is then cooled and 150 ml of ethyl acetate, then 20 ml of a 40% sodium hydroxide solution and 100 ml of water, are added. The product is extracted with ethyl acetate, the organic phase is washed with water and then with a saline solution and finally dried over magnesium sulphate. After evaporating to dryness, there are obtained 5 g (77%) of an orangey oil which crystallizes and which is used as is. M.p.=68° C.

c) Methyl ester of 3-(1-adamantyl)-4-(benzyloxy)benzoic acid 28.6 g (100 mM) of the methyl ester of 3-(1-adamantyl)-4-hydroxybenzoic acid, 41.4 g (300 mM) of dipotassium carbonate and 300 ml of methyl ethyl ketone are introduced into a 1000 ml, three-necked flask maintained under nitrogen and equipped with a magnetic stirrer. 13.06 ml (110 mM) of benzyl bromide are then added to the mixture brought to reflux. The reaction mixture is stirred at reflux for 4 hours. After having cooled, the suspension is filtered and the precipitate is washed with acetone. The filtrate is then evaporated to dryness and there are obtained 39.8 g of an oil which crystallizes. This product is used as is in the continuation of the synthesis. M.p.=126°–128° C.

d) 3-(1-Adamantyl)-4-(benzyloxy)benzoic acid

The compound prepared above is dissolved in 400 ml of 1-butanol and, after addition of 16.8 g (300 mM) of potassium hydroxide pellets, the mixture is brought to reflux for 45 minutes. The reaction mixture is then evaporated to dryness, then taken up in 300 ml of water and acidified with 60 ml of 5N hydrochloric acid. The precipitate is filtered and washed a number of times with water and then dried. There are obtained 35.5 g (98.1%) of 3-(1-adamantyl)-4-(benzyloxy)benzoic acid with a melting point M.p.=251°–253° C.

e) 3-(1-Adamantyl)-4-(benzyloxy)benzoic acid chloride 13.7 g (38 mM) of the acid obtained above and 140 ml of toluene and 0.1 ml of dimethylformamide are introduced into a round-bottomed flask. The mixture is heated to 80° C. and 3 ml (41.8 mM) of thionyl chloride are added dropwise and then the mixture is heated at reflux until evolution of gas has ceased. The mixture is evaporated to dryness and there are thus obtained 14.4 g of 3-(1-adamantyl)-4-(benzyloxy)benzoic acid chloride which is used as is in the following synthesis.

f) 2-Benzyloxy-6-amino-N-[3-(1-adamantyl)-4-(benzyloxy)benzoyl]aniline 4.06 g (19 mM) of 6-amino-2-(benzyloxy)aniline, 2.64 ml (19 mM) of triethylamine and 30 ml of dry THF are introduced into a round-bottomed flask. The mixture is cooled to 4° C. and 7.22 g (19 mM) of the above acid chloride, dissolved in 60 ml of dry tetrahydrofuran (THF), are added dropwise. The mixture is then stirred at 20° C. for 12 hours, the reaction mixture is then poured into water and, after extraction with ethyl acetate, the organic phase is separated by settling, washed with a saline solution and evaporated after drying over magnesium sulphate. The residue obtained is chromatographed on a silica column (eluent: 20% ethyl acetate and 80% hexane) to lead to 7.1 g (67%) of 2-benzyloxy-6-amino-N-[3-(1-adamantyl)-4-(benzyloxy)benzoyl]aniline. M.p.=80°–82° C.

g) 4-Benzyloxy-2-[3-(1-adamantyl)-4-(benzyloxy)phenyl]benzimidazole 6.98 g (12.5 mM) of the amide obtained above are suspended in 60 ml of toluene in a round-bottomed flask and the mixture is heated to 80° C. 2.32 ml (25 mM) of phosphorus oxychloride are then added dropwise. The mixture is stirred at 100° C. for 1 hour and then cooled. After addition of 50 ml of hexane, the precipitate which is formed is filtered and washed with ether. The product is converted into the base form in tetrahydrofuran (THF) by addition of a 45% aqueous sodium hydroxide solution. After stirring, the solution is extracted with ethyl acetate and the organic phase is then separated by settling, dried and evaporated to dryness. There are obtained, by chromatography on a silica column (eluent: 40% ethyl acetate and 60% hexane), 4.3 g (63%) of the expected product. M.p.=109°–111° C.

h) 4-Hydroxy-2-[3-(1-adamantyl)-4-hydroxyphenyl]-benzimidazole 4.1 g (7.6 mM) of the benzyl ether obtained above and 450 ml of a mixture containing 50% acetic acid and 50% dioxane are introduced into the reactor of an autoclave. 346.4 mg of 10% palladium-on-charcoal are added to this solution and, after having purged the reactor with nitrogen, hydrogen is introduced to a pressure of 7 bar. The mixture is stirred at 60° C. for 2 hours. The mixture is then cooled and filtered through Celite. After rinsing the Celite with THF, the filtrate is evaporated to dryness. After chromatography on a silica column (eluent: 30% THF and 70% hexane) and recrystallization from an ethanol/water mixture, there are obtained 1.2 g (44%) of 4-hydroxy-2-[3-(1-adamantyl)-4-hydroxyphenyl]benzimidazole. M.p.=307°–309° C.

Example 2

5-Hydroxy-2-[3-(1-adamantyl)-4-hydroxyphenyl]benzimidazole

A—Process A a) 4-Methoxy-2-nitro-N-[3-(1-adamantyl)-4-methoxybenzoyl]aniline 5.38 g (32 mM) of 2-nitro-4-methoxyaniline and 50 ml of pyridine are introduced into a round-bottomed flask. 9.7 g (32 mM) of 3-(1-adamantyl)-4-methoxybenzoic acid chloride, dissolved in 100 ml of dichloromethane, are added dropwise. At the end of addition, the mixture is brought to reflux for 12 hours. After having cooled, 100 ml of hexane are added and the precipitate obtained is recovered by filtration and washed with a mixture containing 10% ether and 90% hexane and then with water. After drying, there are obtained 12.5 g (89%) of the expected product. M.p.=208°–210° C.

b) 4-Methoxy-2-amino-N-[3-(1-adamantyl)-4-methoxybenzoyl]aniline 11.3 g (25.9 mM) of the nitro derivative prepared above, 110 ml of ethanol and 26.5 g (140 mM) of tin dichloride are introduced into a round-bottomed flask. The mixture is brought to reflux for 2 hours and then evaporated to dryness. The residue is taken up in 200 ml of ethyl acetate and 100 ml of water and 20 ml sodium hydroxide solution. The organic phase is reported by settling, washed with a saturated aqueous disodium carbonate solution and dried over magnesium sulfate. After evaporation to dryness and washing of the residue with a mixture containing 10% ether and 90% hexane, there are obtained 6.6 g (62%) of corresponding product which is used as is in the continuation of the synthesis. M.p.=211°–213° C.

c) 5-Methoxy-2-[3-(1-adamantyl)-4-methoxyphenyl]-benzimidazole

In a way analogous to Example 1(g), there are obtained, from 6.49 g of the above amide, after washing the crude product with ether, 5.8 g (93%) of 5-methoxy-2-[3-(1-adamantyl)-4-methoxyphenyl]benzimidazole with a melting point M.p.=148°–150° C.

d) 5-Hydroxy-2-[3-(1-adamantyl)-4-hydroxyphenyl]-benzimidazole 5.5 g (14.2 mM) of the product prepared in (c) and 25 g of pyridine hydrochloride are introduced into a round-bottomed flask equipped with a stirrer and reflux condenser and which is under a nitrogen flow. The reaction mixture is heated at 200° C. for 3 hours. After having cooled, the mixture is poured into water and, after neutralization with sodium hydroxide solution, the precipitate obtained is filtered and then washed with water. The product is chromatographed on a silica column (eluent: 60% THF and 40% hexane), then recrystallized from dioxane and there are obtained 1.4 g (27%) of 5-hydroxy-2-[3-(1-adamantyl)-4-hydroxyphenyl]benzimidazole. M.p.=241°–243° C.

B—Process B 3.5 g (6.48 mM) of the derivative obtained below in Example 13 are hydrogenated under the conditions described in Example 4 to lead, after the same treatment, to 1.49 g (64%) of 5-hydroxy-2-[3-(1-adamantyl)-4-hydroxyphenyl]benzimidazole, of melting point 240°–245° C.

Example 3

5-Benzyloxy-2-[3-(1-adamantyl)-4-methoxyphenyl]benzimidazole a) 2-Nitro-4-(benzyloxy)aniline 28.87 g (187.5 mM) of 2-nitro-4-hydroxyaniline in 600 ml of methyl ethyl ketone (MEK) are treated with 77.6 g of potassium carbonate and 22.3 ml (187.5 mM) of benzyl bromide. The reaction mixture is heated at reflux for 3 h and is then evaporated to dryness. The evaporation residue is triturated in hexane, is filtered and dried under vacuum. There are thus isolated 40 g (88.9%) of the expected derivative, of melting point 106° C.

b) 2-Amino-4-(benzyloxy)aniline 48.8 g of the nitro derivative obtained in Example 3(a) are placed in 300 ml of 95% ethanol. 16 ml of 20% sodium hydroxide in water are added to the solution. The reaction mixture is heated to reflux and then 52.3 g (800 mM) of zinc powder are added. The reaction mixture is heated at reflux for 4 h. 1.8 g of sodium dithionite are added and the mixture is then filtered while hot and evaporated to dryness. The evaporation residue is chromatographed on silica in the dichloromethane/ethyl acetate (70/30) eluent to lead to 15.7 g (36.7%) of the expected derivative, of melting point 184° C.

c) 2-Amino-4-(benzyloxy)aniline dihydrochloride 7.5 g of nickel are added to a solution of 73.2 g (300 mM) of the amino derivative obtained in Example 3(b) in 900 ml of methanol, the mixture is then heated to reflux and 84.4 ml of hydrazine hydrate are then added. The reaction mixture is heated at reflux with stirring for 1 h 30. After evaporating to dryness, the residue is taken up in 300 ml of THF and acidified with 64 ml of concentrated hydrochloric acid. The precipitate obtained is filtered, rinsed with THF and dried under vacuum to lead to 55.5 g (64.5%) of the expected derivative, of melting point 234° C.

d) 4-Benzyloxy-2-amino-N-[3-(1-adamantyl)-4-methoxybenzoyl]aniline 6.41 g (20 mM) of the chloride of 3-(1-adamantyl)-4-methoxybenzoic acid obtained according to the conditions described for the preparation of 1(e) are dissolved in 60 ml of dry THF and are added dropwise to a solution consisting of 4.28 g (20 mM) of the amine obtained in Example 3(c). The reaction mixture is left stirring at room temperature overnight. After the same treatment as in Example 1(f) followed by chromatography on silica in the ethyl acetate/hexane (40/60) mixture, there are isolated 7.2 g (74.7%) of the expected derivative, of melting point 185° C.

e) 5-Benzyloxy-2-[3-(1-adamantyl)-4-methoxyphenyl]benzimidazole 5.78 g (12 mM) of the amide obtained in Example 3(d) are placed in 60 ml of toluene and are treated with 1.12 ml (12 mM) of phosphorus oxychloride under the conditions described in Example 1(g) to lead, after the same treatment, chromatography on silica in the dichloromethane/methanol (99/1) eluent and trituration in ether, to 4.6 g (82.7%) of the expected derivative, in the form of a beige solid product.

$^1$H NMR: δ ppm (CDCl$_3$): 1.65 (6H, t, adamantyl), 1.93 (9H, s, adamantyl), 3.82 (3H, s, OCH$_3$), 5.01 (2H, s, Bn), 6.85–6.94 (2H, m, Ar), 7.10–7.42 (7H, m, Ar), 7.86–7.91 (2H, d, Ar), 11.29 (1H, NH).

Example 4

5-Hydroxy-2-[3-(1-adamantyl)-4-methoxyphenyl]benzimidazole 4.64 g (10 mM) of the derivative obtained in Example 3 are placed in 300 ml of acetic acid and 300 ml of dioxane and are then hydrogenated at 60° C. under a hydrogen pressure of 7 bar for 3 h in the presence of 0.93 g of palladium-on-charcoal (10%). The reaction mixture is filtered through Celite and evaporated to dryness. The evaporation residue is washed with ether and recrystallized with dioxane and then decoloured while hot with animal charcoal. There are isolated 2.6 g of the expected derivative, of melting point 229.8° C.

Example 5

5-Benzyloxy-2-[3-(1-methylcyclohexyl)-4-(benzyloxy)phenyl]benzimidazole a) 3-(1-Methylcyclohexyl)-4-(benzyloxy)benzoic acid 17.48 g (65 mM) of 2-(1-methylcyclohexyl)-4-bromophenol are placed in 200 ml of MEK and are treated with 27 g (195 mM) of potassium carbonate. The mixture is brought to reflux, 8.5 g (71.5 mM) of benzyl bromide are then added and heating of the mixture at reflux is continued for 4 h. The reaction mixture is filtered. After evaporating the filtrate, the residue is chromatographed on silica in hexane to lead to 16.4 g (70.4%) of 3-(1-methylcyclohexyl)-4-(benzyloxy)-bromobenzoic acid, in the form of a colourless oil.

A solution of 16.15 g (45 mM) of this brominated derivative, in 80 ml of dry THF, is added dropwise to a three-necked flask, under nitrogen, containing 1.2 g (49.5 mM) of magnesium and a crystal of iodine. Gentle reflux is maintained during the addition and then for 1 h after the end of the addition. The reaction mixture is cooled to −40° C. and carbon dioxide gas is then bubbled through. The reaction mixture is poured into water and acidified with 15 ml of 5N HCl. Extraction is carried out with ethyl acetate and the extract is rinsed with water to a pH of 7, dried over magnesium sulphate and evaporated. After recrystallization from the hexane/ether mixture, there are isolated 7.6 g (52.1%) of the expected derivative, of melting point 157° C.

b) 5-Benzyloxy-2-[3-(1-methylcyclohexyl)-4-(benzyloxy)phenyl]benzimidazole 4.08 g (12.6 mM) of the acid obtained in Example 5(a) and 3.23 g (15 mM) of 2-amino-4-(benzyloxy)aniline are placed in 50 ml of orthodichlorobenzene. 50 mg of aluminium chloride are then added, the mixture is heated to 130° C. and 1.54 ml (17.64 mM) of phosphorus trichloride are then added dropwise. The reaction mixture is heated at 130° C. for 2 h, is then poured into water and neutralized by addition of a 2N sodium hydroxide solution. Extraction is carried out with ethyl acetate and the organic phase is rinsed with water, dried over magnesium sulphate and evaporated. The residue is chromatographed on silica in the dichloromethane/methanol (99/1) eluent and recrystallized from an ethanol/water mixture to lead to 2.7 g (42.7%) of the expected derivative, of melting point 209° C.

Example 6

5-Hydroxy-2-[3-(1-methylcyclohexyl)-4-hydroxyphenyl]benzimidazole 2.68 g (5.35 mM) of the compound obtained in Example 5(b) are hydrogenated under the conditions described in Example 4. There are isolated, after chromatography on silica in the dichloromethane/methanol (92/8) eluent, 1.3 g (75%) of the expected derivative, of melting point 180°–185° C.

Example 7

5-Methoxy-2-[3-(1-adamantyl)-4-(benzyloxy)phenyl]benzimidazole a) Methyl 3-(1-adamantyl)-4-(benzyloxy)benzoate 57 g (200 mM) of methyl 3-(1-adamantyl)-4-hydroxybenzoate are treated with benzyl bromide under the conditions described in Example 5(a) to lead to 69.5 g (92.4%) of the expected derivative, of melting point 127° C.

b) 3-(1-Adamantyl)-4-(benzyloxy)benzoic acid 69.5 g (184.8 mM) of the ester obtained in Example 7(a) are placed in 600 ml of n-butanol and are treated with 31.05 g (554.4 mM) of potassium hydroxide. The mixture is stirred under reflux for 1 h and is then evaporated. The evaporation residue is taken up in water and acidified with 60 ml of 10M HCl. The precipitate is filtered and rinsed with water to neutral pH to lead, after drying, to 59.4 g (88.8%) of the expected derivative, of melting point 251° C.

c) 5-Methoxy-2-[3-(1-adamantyl)-4-(benzyloxy)phenyl]benzimidazole 8.69 g (24 mM) of the acid obtained in Example 7(b) and 3.97 g (28.8 mM) of 3,4-diaminoanisole are treated under the conditions described in Example 5(b) to lead, after the same treatment, chromatography on silica in the THF/ethyl acetate (40/60) mixture and recrystallization from an ethanol/water mixture, to 3.3 g (29.7%) of the expected derivative, of melting point 251°–253° C.

Example 8

5-Methoxy-2-[3-(1-adamantyl)-4-hydroxyphenyl]benzimidazole 3.25 g (7 mM) of the derivative obtained in Example 7(c) are hydrogenated under the conditions described in Example 4 to lead to 1.9 g (72.5%) of the expected derivative, of melting point 315°–320° C.

Example 9

5-Benzyloxy-2-[3-benzyloxy-4-(1-adamantyl)phenyl]benzimidazole a) Methyl 3-hydroxy-4-(1-adamantyl)benzoate 12.16 g (80 mM) of methyl 3-hydroxybenzoate and 12.16 g (80 mM) of adamantanol in 160 ml of dichloromethane are treated with a dropwise addition of 4.37 ml of concentrated sulphuric acid. The reaction mixture is stirred at room temperature overnight. The solid residue is washed with water and dried to lead to 18.3 g (79.9%) of the expected derivative, of melting point 244°–246° C.

b) 3-Benzyloxy-4-(1-adamantyl)benzoic acid 18 g (63 mM) of the ester obtained in Example 9(a) are treated with benzyl bromide under the conditions described in Example 5(a) to lead, after the same treatment, to 17.5 g (74%) of methyl 3-benzyloxy-4-(1-adamantyl)benzoate. The derivative obtained is then saponified under the conditions described in Example 7(b) to lead, after the same treatment, to 13.6 g (96.6%) of the expected derivative, of melting point 240° C.

c) 4-Benzyloxy-2-amino-N-[3-benzyloxy-4-(1-adamantyl)benzoyl]aniline 2.7 g (12.7 mM) of 2-amino-4-(benzyloxy)aniline and 5 g (12.7 mM) of the chloride of 3-benzyloxy-4-(1-adamantyl)benzoic acid are treated under the conditions described in Example 1(f) to lead, after the same treatment and chromatography on silica in the ethyl acetate/hexane (30/70) eluent, to 4.2 g (59.3%) of the expected derivative, of melting point 178° C.

d) 5-Benzyloxy-2-[3-benzyloxy-4-(1-adamantyl)phenyl]benzimidazole 4.13 g (7.4 mM) of the amide obtained in Example 9(c) are dissolved in 40 ml of xylene and treated with 1.55 g (8.14 mM) of para-toluenesulphonic acid. The reaction mixture is heated at reflux overnight, is then poured into ice-cold water and brought to a pH of 10 with potassium carbonate. Extraction is carried out with ethyl acetate and the organic phase is rinsed with water, dried over magnesium sulphate and evaporated. There are obtained, after chromatography on silica in dichloromethane, 2.7 g (67.5%) of the expected derivative, of melting point 203° C.

Example 10

5-Hydroxy-2-[3-hydroxy-4-(1-adamantyl)phenyl]benzimidazole 2.5 g (4.63 mM) of the derivative obtained in Example 9 are hydrogenated for 8 h under the conditions described in Example 4 to lead, after the same treatment, followed by chromatography on RP 18 (Merck) in the methanol/water (90/10) eluent, to 1.05 g (62.9%) of the expected derivative, of melting point 250°–252° C.

Example 11

5-Benzyloxy-2-[3-(1-adamantyl)-4-benzyloxy-5-methoxyphenyl]benzimidazole a) Methyl 3-(1-adamantyl)-4-hydroxy-5-methoxybenzoate 12.37 g (68 mM) of methyl 3-methoxy-4-hydroxybenzoate in 150 ml of dichloromethane are treated with 10.33 g (68 mM) of adamantanol and 3.72 ml of concentrated sulphuric acid under the conditions described in Example 9(a). After the same treatment, there are isolated 20.3 g (94.5%) of the expected derivative, of melting point 179° C.

b) 3-(1-Adamantyl)-4-benzyloxy-5-methoxybenzoic acid 18.32 g (58 mM) of the phenol obtained in Example 11(a) are treated with benzyl bromide under the conditions described in Example 5(a). After the same treatment, followed by chromatography on silica in the hexane/ether (90/10) eluent, there are isolated 15.26 g (59.6%) of methyl 3-(1-adamantyl)-4-benzyloxy-5-methoxybenzoate. 15.22 g (37.5 mM) of this ester in 150 ml of methanol are treated with 6.3 g of potassium hydroxide and are heated at reflux overnight. After the same treatment as in Example 1(d), there are isolated 13.7 g (93.2%) of the expected derivative, of melting point 229° C.

c) 5-Benzyloxy-2-[3-(1-adamantyl)-4-benzyloxy-5-methoxyphenyl]benzimidazole 4.94 g (12.6 mM) of the acid obtained in Example 11(b) are treated with a mixture of aluminium chloride and phosphorus trichloride under the conditions described in Example 5(b) to lead, after the same treatment, followed by chromatography on silica in the ethyl acetate/hexane (30/70) mixture, to 2.6 g (36.2%) of the expected derivative, of melting point 143° C.

Example 12

5-Hydroxy-2-[3-(1-adamantyl)-4-hydroxy-5-methoxyphenyl]benzimidazole 2.39 g (4.2 mM) of the derivative obtained in Example 11(c) are hydrogenated under the conditions described in Example 4 to lead, after the same treatment, followed by chromatography on silica in the dichloromethane/methanol (95/5) mixture, to 1 g (61%) of the expected derivative, of melting point 227.2° C.

Example 13

5-Benzyloxy-2-[3-(1-adamantyl)-4-(benzyloxy)phenyl]-benzimidazole a) 2-Amino-4-benzyloxy-N-[3-(1-adamantyl)-4-(benzyloxy)benzoyl]aniline 3.8 g (10 mM) of the acid chloride obtained in Example 8b and 2.14 g (10 mM) of 2-amino-4-(benzyloxy)aniline are treated under the conditions described in Example 1(f) to lead, after the same treatment, followed by recrystallization from ethanol, to 4.8 g (87%) of the expected derivative, of melting point 166°–170° C.

b) 5-Benzyloxy-2-[3-(1-adamantyl)-4-(benzyloxy)-phenyl]benzimidazole 4.5 g (8 mM) of the derivative obtained in Example 13(a) are treated with phosphorus oxychloride under the conditions described in Example 1(g) to lead, after the same treatment, followed by recrystallization from ethanol, to 3.67 g (85%) of the expected derivative, of melting point 265°–275° C.

COMPOSITION EXAMPLES

Example 1: Cream

A cream containing a continuous aqueous phase and corresponding to the following formula was prepared according to the usual methods:

| | |
|---|---|
| 4-Hydroxy-2-[3-(1-adamantyl)-4-hydroxyphenyl]benzimidazole | 1.00 g |
| Cetyl alcohol | 4.00 g |
| Glyceryl monostearate | 2.50 g |
| Stearate of PEG 50 | 2.50 g |
| Petroleum jelly | 10.00 g |
| Methyl parahydroxybenzoate | 0.01 g |
| Propyl parahydroxybenzoate | 0.01 g |
| Demineralized water | 79.98 g |

Example 2: Gel

A gel having the following composition was prepared according to the usual methods:

| | |
|---|---|
| 5-Hydroxy-2-[3-(1-adamantyl)-4-hydroxyphenyl]benzimidazole | 2.00 g |
| Ethyl alcohol (95 volume %) | 20.00 g |
| Hydroxypropyl cellulose | 2.00 g |
| Sterile demineralized water | 76.00 g |

Example 3: Ointment

An ointment having the following composition was prepared according to the usual methods:

| | |
|---|---|
| 4-Hydroxy-2-[3-(1-adamantyl)-4-hydroxyphenyl]benzimidazole | 5.00 g |
| Triglycerides of capric and caprylic acids | 49.00 g |
| Petroleum jelly | 46.00 g |

Example 4: Cream

A cream containing a continuous aqueous phase and having the following composition was prepared according to the usual methods:

| | |
|---|---|
| 5-Hydroxy-2-[3-(1-adamantyl)-4-hydroxyphenyl]benzimidazole | 0.10 g |
| Mixture of emulsifying lanolin alcohols and of hydrocarbon-based refined oils and waxes sold under the name of "Anhydrous Eucerine" by the Company BDF | 40.00 g |
| Methyl parahydroxybenzoate | 0.07 g |
| Propyl parahydroxybenzoate | 0.08 g |
| Demineralized water | 59.75 g |

Example 5: Gelatin Capsule

A powder having the following composition was prepared:

| | | |
|---|---|---|
| 5-Hydroxy-2-[3-(1-adamantyl)-4-hydroxyphenyl]benzimidazole | | 0.125 g |
| Maize starch | | 0.060 g |
| Lactose | q.s. for | 0.300 g |

The product obtained is packaged in a gelatin capsule whose wall is composed of gelatin, $TiO_2$ and a preserving agent.

We claim:

1. Benzimidazole derivatives, wherein said benzimidazole derivatives correspond to the following general formula:

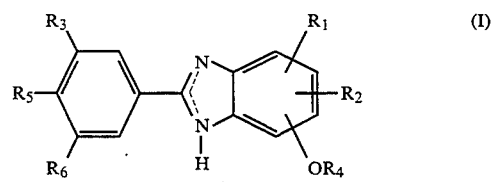

(I)

in which:
- $R_1$ and $R_2$ represent a hydrogen atom, a lower alkyl radical, an $OR_4$ radical, a lower fluoroalkyl radical or a halogen atom,
- $R_3$ represents a hydrogen atom, a lower alkyl radical, a halogen, a hydroxyl or a lower alkoxy radical having from 1 to 6 carbon atoms,
- $R_4$ represents a hydrogen atom, a lower alkyl radical, a benzyl radical, or a

PO$_3$H or SO$_3$H radical or an amino acid residue,

R$_7$ represents a lower alkyl radical, a lower alkoxy radical having from 1 to 6 carbon atoms, the —(CH$_2$)$_n$—COOH radical, n=1 to 6, or the

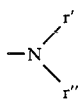

radical, r' and r" representing a hydrogen atom or a lower alkyl radical or r' and r", taken together, form, with the nitrogen atom, a 5- or 6-membered heterocycle optionally interrupted by a heteroatom, R$_5$ and R$_6$, which are different, represent the OR$_8$ radical or a mono- or polycyclic cycloalkyl radical having from 5 to 12 carbon atoms, linked to the phenyl ring via a tertiary carbon;

R$_8$ represents a hydrogen atom, a lower alkyl radical, an acyl radical having from 2 to 7 carbon atoms, a benzyl radical optionally substituted by one or a number of halogen atoms or the benzoyl radical, and the salts of the said compounds obtained by addition of a pharmaceutically acceptable acid or base.

2. Compounds according to claim 1, wherein the lower alkyl radical is selected from the group consisting of methyl, ethyl, isopropyl, butyl, 1-methylpropyl, 1-ethylpropyl, tert-butyl, 1,1-dimethylpropyl and 1-methyl-1-ethylpropyl radicals.

3. Compounds according to claim 1, wherein the lower fluoroalkyl radical is a radical having from 1 to 6 carbon atoms and from 1 to 5 fluorine atoms.

4. Compounds according to claim 1, wherein the halogen atom is chlorine, bromine or fluorine.

5. Compounds according to claim 1, wherein the amino acid residue is a residue deriving from lysine, glycine or aspartic acid.

6. Compounds according to claim 1, wherein the alkoxy radical is selected from the group consisting of methoxy, ethoxy, isopropoxy and butoxy radicals.

7. Compounds according to claim 1, wherein the mono- or polycyclic cycloalkyl radical having from 5 to 12 carbon atoms, linked to the phenyl ring via a tertiary carbon, is selected from the group consisting of 1-adamantyl and 1-methylcyclohexyl radicals.

8. Compounds according to claim 1, wherein the acyl radical having from 2 to 7 carbon atoms is selected from the group consisting of acetyl, propionyl, butyryl, isobutyryl, valeryl and pivalyl radicals.

9. Compounds according to claim 1, wherein the r' and r" radicals, taken together, form a heterocycle selected from the group consisting of piperidino, morpholino, pyrrolidino and piperazino radicals, optionally substituted in position 4 by a lower alkyl radical.

10. Compounds according to claim 1 wherein said compounds are selected from the group consisting of:
4-hydroxy-2-[3-(1-adamantyl)-4-hydroxyphenyl]benzimidazole,
5-hydroxy-2-[3-(1-adamantyl)-4-hydroxyphenyl]benzimidazole,
5-benzyloxy-2-[3-(1-adamantyl)-4-methoxyphenyl]benzimidazole,
5-hydroxy-2-[3-(1-adamantyl)-4-methoxyphenyl]benzimidazole,
5-benzyloxy-2-[3-(1-methylcyclohexyl)-4-(benzyloxy)phenyl]benzimidazole,
5-hydroxy-2-[3-(1-methylcyclohexyl)-4-hydroxyphenyl]benzimidazole,
5-methoxy-2-[3-(1-adamantyl)-4-(benzyloxy)phenyl]benzimidazole,
5-methoxy-2-[3-(1-adamantyl)-4-hydroxyphenyl]benzimidazole,
5-benzyloxy-2-[3-benzyloxy-4-(1-adamantyl)phenyl]benzimidazole,
5-hydroxy-2-[3-hydroxy-4-(1-adamantyl)phenyl]benzimidazole,
5-benzyloxy-2-[3-(1-adamantyl)-4-benzyloxy-5-methoxyphenyl]benzimidazole,
5-hydroxy-2-[3-(1-adamantyl)-4-hydroxy-5-methoxyphenyl]benzimidazole,
5-benzyloxy-2-[3-(1-adamantyl)-4-(benzyloxy)phenyl]benzimidazole,
5-methoxy-2-[3-(1-adamantyl)-4-methoxyphenyl]benzimidazole,
5-acetoxy-2-[3-(1-adamantyl)-4-acetoxyphenyl]benzimidazole,
5-acetoxy-2-[3-(1-adamantyl)-4-hydroxyphenyl]benzimidazole.

11. Pharmaceutical composition, wherein said composition contains, in a vehicle suitable for administration enterally, parenterally, topically or ocularly, at least one compound of formula (I) according to claim 1.

12. Composition according to claim 11, wherein said composition is provided in a form suitable for topical application and contains from 0.005% to 10% by weight of compounds of formula (I).

13. Method of treatment or prevention of at least one of inflammatory and immuno-allergic conditions, comprising administering to a patient suffering at least one of said conditions a therapeutically effective amount of a compound according to claim 1.

14. Cosmetic composition intended to prevent unhealthy appearance of the skin, wherein said composition contains, in a suitable cosmetic vehicle, at least one compound of formula (I) according to claim 1.

15. Cosmetic composition according to claim 14, wherein said composition contains the compound of formula (I) at a concentration between 0.001 and 5% with respect to the total weight of the composition.

16. A method according to claim 13, wherein the pharmaceutical composition is administered at a daily dose of the active compound of between 0.01 to 100 mg/kg of body weight.

* * * * *